United States Patent [19]

Murakami et al.

[11] 4,036,834
[45] July 19, 1977

[54] DERIVATIVES OF 7-(α-HYDROXY-SUBSTITUTED PYRIDYL CARBOXAMIDO-α PHENYL-ACETAMIDO-3-SUBSTITUTED THIO METHYL Δ³-CEPHEM-4-CARBOXYLIC ACID

[75] Inventors: Masuo Murakami, Tokyo; Masaru Iwanami, Yokohama; Ichiro Isaka, Hoya; Yoshinobu Nagano, Niiza; Masaharu Fujimoto, Tokyo; Tetsuya Maeda, Urawa, all of Japan

[73] Assignee: Yamanouchi Pharmaceutical Co., Ltd., Tokyo, Japan

[21] Appl. No.: 620,552

[22] Filed: Oct. 8, 1975

[30] Foreign Application Priority Data

Oct. 11, 1974  Japan .................. 49-116976

[51] Int. Cl.² ............................ C07D 501/36
[52] U.S. Cl. ............................ 260/243 C; 424/246
[58] Field of Search ..................... 260/243 C

[56] References Cited

U.S. PATENT DOCUMENTS

| | | | |
|---|---|---|---|
| 3,843,642 | 10/1974 | Jackson et al. | 260/243 C |
| 3,946,015 | 3/1976 | Goel | 260/243 C |
| 3,948,903 | 4/1976 | Doub et al. | 260/243 C |

FOREIGN PATENT DOCUMENTS 2,362,816  6/1974  Germany

OTHER PUBLICATIONS

CA, vol. 81, Teruya et al., p. 536, Abst. 105,537f (1974).

*Primary Examiner*—Nicholas S. Rizzo
*Assistant Examiner*—David E. Wheeler
*Attorney, Agent, or Firm*—Burgess, Ryan and Wayne

[57] ABSTRACT

Novel 7-(α-hydroxy-substituted pyridylcarboxamido-α-phenylacetamido)-3-substituted thiomethyl-Δ³-cephem-4-carboxylic acid derivatives are disclosed. The compounds of this invention have high water solubility and show excellent antibacterial activities against various strains of Pseudomonas and Proteus.

8 Claims, No Drawings

DERIVATIVES OF 7-(α-HYDROXY-SUBSTITUTED PYRIDYL CARBOXAMIDO-α PHENYL-ACETAMIDO-3-SUBSTITUTED THIO METHYL Δ³-CEPHEM-4-CARBOXYLIC ACID

BACKGROUND OF THE INVENTION

1. Field of the Invention

The present invention relates to novel 7-(α-hydroxy-substituted pyridylcarboxamido-α-phenylacetamido)-3-substituted thiomethyl-Δ³-cephem-4-carboxylic acid derivatives. More particularly, the invention relates to 7-(α-hydroxy-substituted pyridylcarboxamido-α-phenylacetamido)-3-substituted thiomethyl-Δ³-cephem-4-carboxylic acid derivatives shown by general formula V:

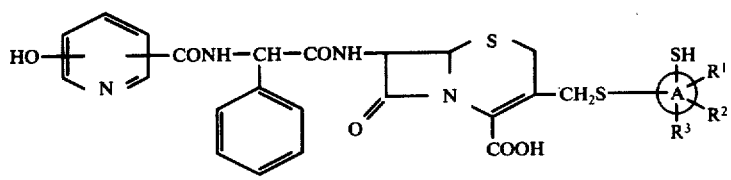

wherein A represents a 6-membered heterocyclic ring having one sulfur atom or 2 or 3 nitrogen atoms and the remaining being carbon atoms and $R^1$, $R^2$ and $R^3$, which may be the same or different each represents a hydrogen atom, a lower alkyl group, a lower alkylthio group, an amino group, a lower alkanoylamido group, or an oxo group
and the pharmacologically acceptable salts thereof.

2. Description of the Prior Art

A series of cephalosporin derivatives shown by general formula:

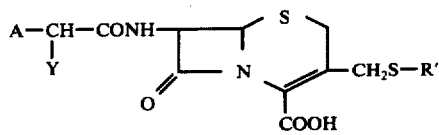

wherein R' represents a 5- or 6-membered heterocyclic nucleus having in the nucleus 1–4 nitrogen atom, oxygen atoms, or sulfur atoms
are disclosed in Belgian Patent No. 776,222. In these cephalosporin derivatives of the above formula are included and the cephalosporin derivatives having a heterocyclic acyl group attached to the amino group of the α-aminophenylacetamido group at the 7-position as shown by the general formula:

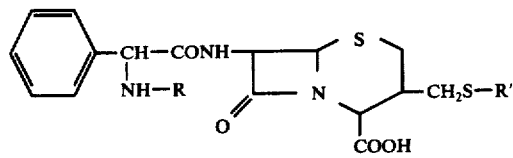

wherein R represents a heterocyclic acyl group which may be substituted by a methyl group and R' has the same meaning as in the above indicated general formula.

However, the aforesaid Belgian patent does not disclose NH—R type compounds having a heterocyclic acyl group which may have a methyl group as the aforesaid cephalosporin derivatives. Furthermore, there are neither disclosures nor suggestions regarding the 5- or 6-membered heterocyclic nuclei substituted by an -SH group in the explanation of group R' described in the specification of the Belgian patent.

SUMMARY OF THE INVENTION

According to the present invention, there are provided novel 7-(α-hydroxy-substituted pyridylcarboxamido-α-phenylacetamido)-3-substituted thiomethyl-Δ³-cephem-4-carboxylic acid derivatives represented by general formula V indicated above.

The aforesaid compounds of this invention show wide antibacterial activities against gram positive bacteria and gram negative bacteria, and, in particular, excellent antibacterial activities against strains of Pseudomonas and Proteus. Therefore, they can be administered to human beings and animals as agents for treating various diseases infected by these bacteria.

Cephalosporin derivatives effective against Pseudomonas strains have not hitherto been known but by the discovery of the cephalosporin derivatives of this invention, it becomes possible to treat the disease caused by these strains. In particular, since the compounds of this invention have high water solubility, they are suitable for administration by injection.

DESCRIPTION OF THE PREFERRED EMBODIMENTS

In the cephalosporanic acid derivatives of this invention represented by general formula V, examples of the herein described 6-membered ring having one sulfur atom represented by A are a 2H-thiopyran ring and a 4H-thiopyran ring and examples of the 6-membered ring having 2 or 3 nitrogen atoms are a pyridine ring, a pyridazine ring, a pyrazine ring, a pyrimidine ring, etc. These rings may be partially saturated or quaternarized. Among the aforesaid rings represented by A, the 4H-4-thiopyrone ring, the pyrimidine ring, etc., are preferable.

All of the substitutents $R^1$, $R^2$, and $R^3$ in general formula V are not always present in the compound of the formula. In other words, the presences of these substitutents are restricted by the number of the nitrogen atoms constituting the ring A. For example, when ring A is triazine, the substituent is restricted to one and when the ring is a pyrimidine ting, the substituent is restricted to two.

Now, in substituents $R^1$, $R^2$, and $R^3$ of general formula V, examples of the lower alkyl group are a methyl group, an ethyl group, an iso-butyl group, a sec-butyl group, etc. Examples of the lower alkylthio group are a methylthio group, an ethylthio group, a propylthio group, etc. Examples of the lower alkanoylamido group are an acetamido group, a propionamido group, an isovalerylamido group, etc.

Also, examples of the pyridinecarboxylic acid constituting the pyridylcarboxamido group of the compound of this invention are nicotinic acid, iso-nicotinic acid, picolinic acid, etc., and a hydroxy substituent may be at any position of the acid. For example, there are illustrated 4-hydroxynicotinic acid, 4-hydroxypicolinic acid, 2-hydroxynicotinic acid, etc.

Typical examples of the compounds of this invention are, for example, 7-[(α-4-hydroxynicotinoylamido)-α-phenylacetamido]-3-(4-mercapto-2-methylpyrimidin-6-ylthiomethyl)-Δ³-cephem-4-carboxylic acid, 7-[(α-4-hydroxynicotinoylamido)-α-phenylacetamido]-3-(2-mercapto-3,5-dimethyl-4-oxo-4H-thiopyran-6-ylthiomethyl)-Δ³-cephem-4-carboxylic acid, 7-[(α-2-hydroxyisonicotinoylamido)-α-phenylacetamido]-3-(2-acetamido-4-mercapto-1,3,5-triazin-6-ylthiomethyl)-Δ³-cephem-4-carboxylic acid, 7-[(α-4-hydroxynicotinoylamido)-α-phenylacetamido]-3-(4-mercaptopyrimidin-6-ylthiomethyl)-Δ³-cephem-4-carboxylic acid, 7-[(α-4-hydroxynicotinoylamido)-α-phenylacetamido]-3-(4-mercapto-2-methylthiopyrimidin-6-ylthiomethyl)-Δ³-cephem-4-carboxylic acid, 7-[(α-4-hydroxynicotinoylamido)-α-phenylacetamido]-3-(2-amino-4-mercaptopyrimidin-6-ylthiomethyl)-Δ³-cephem-4-carboxylic acid, and 7-[(α-4-hydroxynicotinoylamido)-α-phenylacetamido]-3-(3-mercaptopyridazin-6-ylthiomethyl)-Δ³-cephem-4-carboxylic acid.

The compounds of this invention shown by general formula V are all novel compounds and are prepared by reacting cephaloglycin shown by formula I

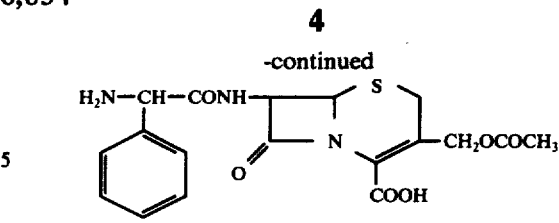

-continued

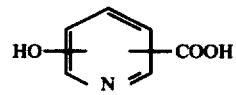

and the hydroxy-substituted pyridinecarboxylic acid represented by formula II

II or the reactive derivative of the carboxy group thereof to form the 7-[(α-hydroxy-substituted pyridyl carboxamido-α-phenylacetamido]-cephalosporanic acid shown by general formula III

III

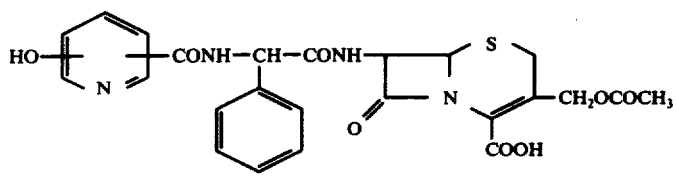

and then reacting the product and the dimercaptoheterocyclic compound represented by general formula IV

IV

wherein R¹, R², and R³ have the same meaning as in formula V or the alkali metal salt thereof.

The aforesaid reaction is shown by the following reaction formula:

I (Cephaloglycin)

Step 1. ↓      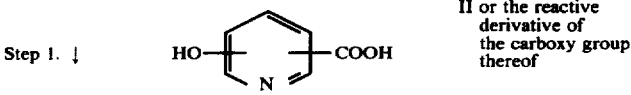

II or the reactive derivative of the carboxy group thereof

III

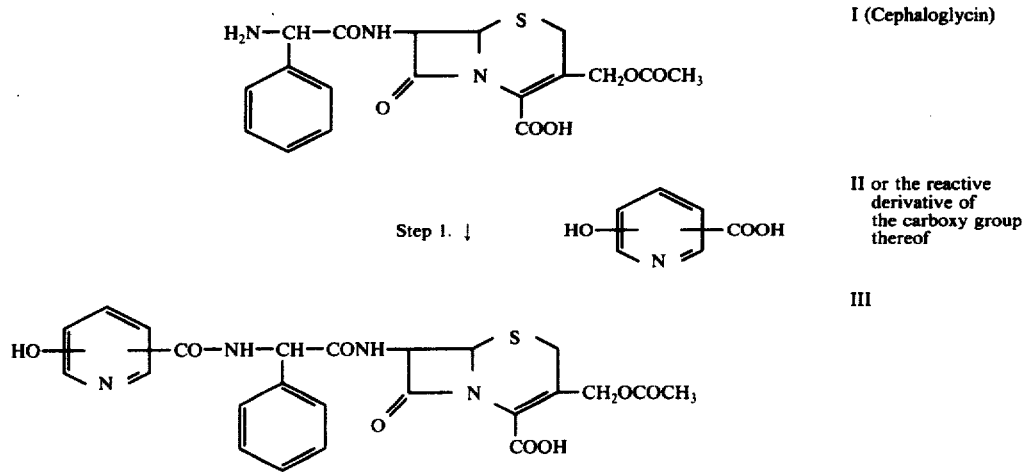

Step 2. ↓      

IV or the alkali metal salt thereof

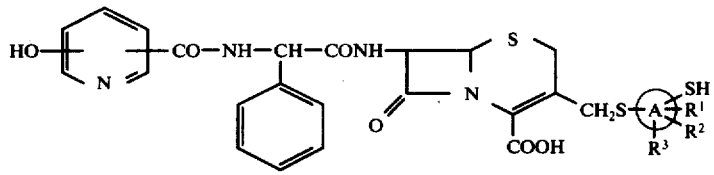

in the above formulae, $R^1$, $R^2$, and $R^3$ have the same meaning as above.

The reaction of Step 1 in the above reaction scheme is carried out by reacting cephaloglycin of formula I and an equimolar amount or an excessive amount of the compound of formula II or a reactive derivative thereof. When the compound of formula II is used in the free state or a salt state thereof, it is preferable to carried out the reaction in the presence of a condensing agent, such as N,N-dichlorohexylcarbodiimide, trialkyl phosphate, phosphorus oxyhalide, phosphorus trihalide, thionyl halide, and oxalyl chloride. According to the combination of the compound of formula II and the condensating agent, for example, when the combination with the condensing agent such as phosphorus trihalide, thionyl halide, etc., is selected, the compound of formula II is introduced into the reaction system after blocking the hydroxyl group with a blocking group such as a benzyloxycarbonyl group and the blocking group may be released from the compound of formula III or V having a blocked hydroxyl group, preferably the compound of formula III by a known method such as catalytic hydrogenation.

Examples of the preferred reactive derivatives of the compound shown by formula II are for example, an acid halide; an acid azide; an acid anhydride; a mixed acid anhydride such as alkylcarboxylic acid mixed acid anhydride, alkylphosphoric acid mixed acid anhydride, dialkylphosphorous acid mixed acid anhydride, and sulfuric acid mixed acid anhydride; an acid amide with imidazole; and an active ester such as p-nitrophenyl ester.

When the alkylcarboxylic acid mixed acid anhydride or the acid halide is used as the reactive derivative, the reaction is carried out under cooling or at room temperature in ordinary organic solvent such as acetone, tetrahydrofuran, dimethylformamide, chloroform, dichloromethane, hexamethyl phosphoramide, etc., or a mixed solvent of them in the presence of a base such as triethylamine, dimethylaniline, etc.

Furthermore, when the compound of formula II is used as a free state or a state of salt thereof, the reaction is carried out in the presence of a condensing agent such as N,N-dicyclohexylcarbodiimide, triethyl phosphate, phosphorus oxychloride, phosphorus trichloride, thionyl chloride, oxalyl chloride, etc.

The compound of formula III thus formed can be isolated from the reaction mixture or purified by ordinary chemical operation such as extraction, recrystallization, etc., but as the case may be the reaction mixture containing the compound of formula III may be introduced to the subsequent reaction system for the reaction with the compound of formula IV without isolation or purification of said compound.

The reaction of step 2 is carried out by reacting the compound of formula III and about an equimolar amount or a slightly excessive amount of the compound of formula IV in, ordinarily, an inert organic solvent such as acetone, ether, chloroform, nitrobenzene, dimethyl sulfoxide, dimethylformamide, methanol, ethanol, or a mixed solvent of them. Also, the reaction is carried out in a neutral or alkaline state in the presence of a basic material such as an alkali metal hydroxide, an alkali metal carbonate, triethylamine, etc.

The reaction sequence of step 1 and step 2 described above may be reversed, that is, the reaction of step 2 may be first carried out and then the reaction of step 1 may be followed.

The subject product of formula V thus formed can be separated and purified by ordinary chemical operations such as extraction, recrystallization, etc. Furthermore, the compound of formula V may be converted into the salt of an inorganic base such as an alkali metal, ammonia, etc., or an organic base such as triethylamine, diethanolamine, lysine, ornithine, etc.

Now, for illustrating the excellent pharmacological effects of the compounds of this invention, the values of MIC ($\gamma$/ml) of the compounds against various bacteria are shown in the following table, the compounds of this invention are shown by example numbers.

Table

| Bacteria No. | Example No. | | | | | | | Cephalexin | Cephaloglycin | Cephazolin | Cephalothin | C-1* | C-2* |
|---|---|---|---|---|---|---|---|---|---|---|---|---|---|
| | 1 | 2 | 3 | 4 | 5 | 6 | 7 | | | | | | |
| 1 | 0.19 | 0.19 | 0.19 | 0.19 | <0.09 | 0.19 | 0.78 | 30 | 25 | 3.13 | | 3.13 | 6.25 |
| 2 | 0.78 | 1.56 | 0.39 | 6.25 | 0.78 | 12.5 | 0.39 | 30 | 100 | 25 | 12.5 | | |
| 3 | 0.39 | 0.39 | 0.78 | 0.39 | 0.19 | 1.56 | 0.78 | | | 100 | 6.25 | 12.5 | 25 |
| 4 | 100 | 12.5 | 12.5 | 50 | 25 | 100 | 25 | >100 | >100 | >100 | >100 | >100 | >100 |
| 5 | 50 | 12.5 | 12.5 | 50 | 25 | 50 | 12.5 | | >100 | >100 | >100 | >100 | >100 |
| 6 | 25 | 12.5 | 6.25 | 50 | 6.25 | 12.5 | 12.5 | | >100 | >100 | | >100 | >100 |
| 7 | 6.25 | 6.25 | 12.5 | 6.25 | 3.13 | 6.25 | 25 | 10 | 100 | 1.56 | 3.13 | 50 | 100 |
| 8 | 6.25 | 3.13 | 12.5 | 12.5 | 3.13 | 6.25 | 12.5 | 3 | 25 | 1.56 | 0.78 | 12.5 | 12.5 |
| 9 | 0.39 | 0.19 | 3.13 | 0.39 | <0.09 | 0.19 | 0.78 | 6.25 | 3 | 1.56 | 1.56 | >100 | >100 |
| 10 | 0.39 | 0.19 | 0.78 | 0.78 | 0.39 | 0.39 | 0.39 | 6.25 | 3 | 1.56 | 0.39 | | |
| 11 | 6.25 | 12.5 | 6.25 | 12.5 | 6.25 | 12.5 | 12.5 | 6.25 | 3 | 1.56 | 6.25 | 50 | 50 |
| 12 | 12.5 | 12.5 | 12.5 | 12.5 | 6.25 | 12.5 | 25 | 6.25 | 10 | 1.56 | 6.25 | 100 | 100 |
| 13 | 0.39 | 0.19 | 0.19 | 0.39 | 0.19 | 0.78 | 0.39 | 0.78 | 1 | 0.19 | | 3.13 | 3.13 |
| 14 | 0.39 | 0.39 | 0.78 | 0.78 | 0.39 | 0.78 | 0.19 | 0.78 | 0.3 | 0.19 | <0.09 | 3.13 | 1.56 |
| 15 | 3.13 | 3.13 | 1.56 | 6.25 | 3.13 | 3.13 | 0.78 | 1.56 | 0.3 | 0.19 | | 1.56 | 1.56 |
| 16 | 0.39 | 0.39 | 1.56 | 1.56 | 0.78 | 0.78 | 0.19 | 1.56 | 1 | 0.19 | 0.19 | | |
| 17 | 1.56 | 3.13 | 6.25 | 6.25 | 3.13 | 3.13 | 0.78 | 6.25 | 3 | 0.78 | 0.39 | | |

Table-continued

| Bacteria No. | Example No. | | | | | | | Contrast | | | | | |
|---|---|---|---|---|---|---|---|---|---|---|---|---|---|
| | 1 | 2 | 3 | 4 | 5 | 6 | 7 | Cepha-lexin | Cepha-loglycin | Cepha-zolin | Cepha-lothin | C-1* | C-2* |
| 18 | 6.25 | 6.25 | 12.5 | 6.25 | 6.25 | 6.25 | 3.13 | 12.5 | 3 | 1.56 | 0.39 | | |

*C-1: 7-(α-nicotinoylamido-α-phenylacetamido)-3-(1-methyl-1H-tetrazole-5-ylthiomethyl)-Δ³-cephem-4-carboxylic acid
C-2: 7-(α-nicotinoylamido-α-phenylacetamido)-3-(2-methyl-1,3,4-thiadiazole-5-ylthiomethyl-Δ³-cephem-4-carboxylic acid
(The compounds C-1 and C-2 are included within the conception of Belgian Patent 776,222, but they are not practically disclosed therein.)

Identity of the bacteria shown in the above Table.
1: Proteus vulgaris OXK US
2: Proteus vulgaris OX 19US
3: Proteus mirabilis IFM OM-19
4: Pseudomonas aeruginosa ATCC 8689
5: Pseudomonas aeruginosa 99 (Gentamycin resistant)
6: Pseudomonas ovalis IAM 1002
7: Escherichia coli Kauffman 0-1
8: Klebsiella pneumoniae ATCC 10031
9: Salmonella typhi H901W
10: Salmonella enteritidis
11: Shigella flexnori 2a 1675
12: Shigella sonnei II 37148
13: Bacillus megatherium 10778
14: Bacillus subtilis ATCC 6633
15: Micrococcus flavus ATCC 10240
16: Staphylococcus aureus 209P
17: Staphylococcus Shimanishi
18: Staphylococcus Onuma Also, since the compounds of this invention possess high solubility in water, they are quite suitable for administration as injections. Then, the experimental results showing the excellent water solubility of the compounds of this invention are illustrated in the following table, the results being the observation results by the naked eyes of the solutions thereof in each concentration as shown in the table.

| | Concentration | | | |
|---|---|---|---|---|
| | 1% | 5% | 10% | 20% |
| Example 2 | clear | clear | clear | slightly turbid |
| Example 3 | clear | clear | clear | clear |
| Contrast* | clear | slightly turbid | turbid | gelled |

(*): 7-(α-nicotinoylamido-α-phenylacetamido)-3-(2-amino-4-chloropyridin-6-ylthiomethyl)-Δ³-cephem-carboxylic acid.

Now, the invention will further be illustrated by the following examples.

EXAMPLE 1-a

In 40 ml. of dichloromethane was suspended 1.4 g. of 4-hydroxynicotinic acid and after adding 1.4 ml. of triethylamine to the suspension, the mixture was stirred for 30 minutes at room temperature to form an almost transparent solution. The solution was cooled to 0°–5° C. and 10 ml. of dichloromethane containing 0.73 ml. of thionyl chloride was added dropwise to the solution at the same temperature. Thereafter, the mixture was stirred for one hour at room temperature to provide a suspension of 4-hydroxynicotinoyl chloride.

In 100 ml. of dichloromethane was suspended 4.25 g. of cephalo glycin monohydrate and then 2.8 ml. of triethylamine was dissolved therein. Furthermore, 5 g. of anhydrous magnesium sulphate was added to the system and after stirring the mixture for about 10 minutes at room temperature, the mixture was filtered to provide a solution of cephaloglycin triethylamine salt. The solution was cooled to −20° C. and the suspension of 4-hydroxynicotinoyl chloride prepared above was added dropwise to the solution with stirring. Thereafter, the cooling bath was removed to raise the temperature up to room temperature and the mixture was stirred for about one hour at room temperature.

The reaction mixture obtained was concentrated at low temperature under reduced pressure and the solid residue formed was dissolved in 100 ml. of cold water. When the pH of the solution was adjusted to 2 with hydrochloric acid, white crystals were precipitated, which were recovered by filtration, washed with water and a small amount of acetone, and then dried.

The crystals thus recovered were dissolved in 30 ml. of dimethylformamide and insoluble matters formed were filtered off. Then, a n-butanol solution of 30% potassium 2ethylhexanoate was added to the filtrate until the precipitation ceased.

Furthermore, 100 ml. of ether was added to the suspension and after allowing to stand the mixture for a while, the precipitates were recovered by filtration and washed with acetone. Then, by purifying the precipitates by dissolving them in water-containing dimethylformamide followed by filtration and reprecipitating with the addition of acetone, 1.35 g. of potassium 7-D-[α-(4-hydroxypyridine-3-carbo x amido)-α-phenylacetamido]cephalosporanate was obtained as the yellowish brown powdery crystals.

Melting point 195°–202° C. (decomp.)

Infrared absorption spectra: $\nu_{max}^{KBr}$cm$^{-1}$: 3400 (NH, OH), 1760 (β-lactam), 1740 (acetate) 1655 (amide), 1600 (carboxylate)

Nuclear magnetic resonance spectra (CD$_3$OD + D$_6$—DMSO)
δ  1.97 (3H, CH$_3$COO—),

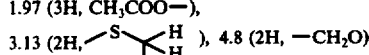

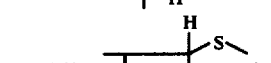

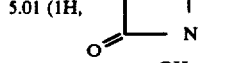

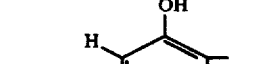

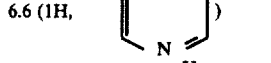

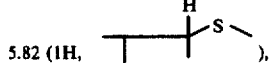

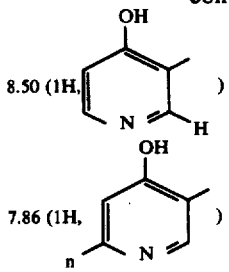

8.50 (1H, )

7.86 (1H, )

EXAMPLE 1-b

A mixture of 500 mg. of sodium 7-[D-α-(4-hydroxynicotinoylamido)-α-phenylacetamido]cephalosporanate, 263 mg. of 3,6-dimercaptopyridazine, 153 mg. of sodium hydrogencarbonate, and 35 ml. of water was heated tp 50°-55° C. for 22 hours with stirring. After the reaction was over, the reaction mixture was filtered and the filtrate was adjusted to pH about 2 with 1 normal hydrochloric acid under ice cooling. The precipitates thus formed were recovered by filtration, washed with water and then ether, and dried under reduced pressure to provide 400 mg. of 7-[D-α-(4-hydroxynicotinoylamido)-α-phenylacetamido]-3-(3-mercaptopyridazin-6-yl)thiomethyl-Δ³-cephem-4-carboxylic acid.

Infrared absorption spectrum: $\nu_{max}^{KBr}$cm.$^{-1}$: 1775 (β-lactam).

Nuclear magnetic resonance spectra (D₆-DMSO): δ(ppm): 3.53 (2H), 4.08 (2H), 5.01 (1H), about 5.73 (1H), 5.83 (1H), 6.43 (1H), 7.33 (7H), 7.80 (1H), 8.44 (1H), 9.41 (1H).

EXAMPLE 2

A mixture of 0.5 g. of 7-[D-α-(4-hydroxynicotinoylamido)-α-phenylacetamido]cephalosporanic acid, 0.188 g. of 2-methyl-4,6-dimercaptopyrimidine, 0.21 g. of sodium hydrogencarbonate, and 40 ml. of water was heated to 50°-55° C. for 22 hours with stirring. After the reaction was over, the reaction mixture was filtered and the filtrate was adjusted to pH about 2 with 1 normal hydrochloric acid under ice cooling. The precipitates thus formed were recovered by filtration, washed with water and then ether, and dried under reduced pressure to provide 0.36 g. of 7-[D-α-(4-hydroxynicotinoylamido)-α-phenylacetamido]-3-(2-methyl-4-mercaptopyrimidin-6-yl) thiomethyl-Δ³-cephem-4-carboxylic acid.

Infrared absorption spectrum: $\nu_{max}^{KBr}$cm.$^{-1}$: 1778 (β-lactam).

Nuclear magnetic resonance spectra (D₆-D MSO): δ(ppm): 2.39 (3H), 3.49 (2H), 3.97 (1H), 4.45 (1H), 5.03 (1H), about 5.75 (1H), 5.86 (1H), 6.47 (1H), 7.01 (1H), 7.40 (5H), 7.85 (1H), 8.47 (1H), 9.46 (1H).

EXAMPLE 3

In 50 ml. of water were suspended 0.8 g. of 7-[D-β-(4-hydroxynicotinoylamido)-β-phenylacetamido]cephalosporanic acid and 0.31 g. of 2,6-dimercapto-3,5-dimethyl-4-oxo-4H-thiopyran and after adding thereto 0.45 g. of sodium hydrogencarbonate, the mixture was heated to 55° C. for 23 hours with stirring. After the reaction was over, insoluble matters formed were filtered off from the reaction mixture and then a 5% aqueous solution of hydrochloric acid was added to the filtrate to adjust the pH thereof to 1. The precipitates thus formed were recovered by filtration, washed sufficiently with water and then with ether, and dried over phosphorus pentoxide under reduced pressure to provide 0.7 g. of the powder of 7-[D-α-(4-hydroxynicotinoylamido)-α-phenylacetamido]-3-(3,5-dimethyl-6-mercapto-4-oxo-4H-thiopyran-2-yl)thiomethyl-Δ³-cephem-4-carboxylic acid.

Infrared absorption spectra: $\nu_{max}^{KBr}$cm.$^{-1}$: 1776 (β-lactam), 1660 (acidamide)

Nuclear magnetic resonance spectrum (D₆-DMSO): δ(ppm): 2.14 (6H, dimethyl on thiopyrone ring).

EXAMPLE 4

In 38 ml. of water were suspended 0.6 g. of 7-[D-α-(4-hydroxynicotinoylamido)-β-phenylacetamido]cephalosporanic acid and 0.23 g. of 2-acetamido-4,6-dimercapto-1,3,5-triazine and after adding thereto 0.32 g. of sodium hydrogencarbonate, the mixture was heated to 55° C. for 18 hours with stirring. After the reaction was over, insoluble matters formed were filtered off from the reaction mixture and a 5% aqueous solution of hydrochloric acid was added to the filtrate to adjust the pH of it to 2. The precipitates formed were recovered by filtration, washed sufficiently with water, and dried over phosphorus pentoxide to provide 0.35 g. of the powder of 7-[D-α-(4-hydroxynicotinoylamido)-α-phenylacetamido]-3-(4-mercapto-6-acetylamino-1,3,5-triazin-2-yl)thiomethyl-Δ³-cephem-4-carboxylic acid.

Infrared absorption spectra: $\nu_{max}^{KBr}$cm.$^{-1}$: 1776 (β-lactam), 1652 (acidamide).

Nuclear magnetic resonance spectrum (D₆-DMSO): δ(ppm): 2.48 (3H, -NHCOCH₃).

EXAMPLE 5

A mixture of 550 mg. of sodium 7-[D-α-(4-hydroxynicotinoylamido)-α-phenylacetamido]cephalosporanate, 220 mg. of 4,6-dimercaptopyrimidine, 150 mg. of sodium hydrogencarbonate, and 50 ml. of water was stirred for 22 hours at 55° C. The reaction mixture thus obtained was filtered and 1 normal hydrochloric acid was added to the filtrate under ice cooling to adjust the pH to 1. Then, the precipitates formed were recovered by filtration, washed with water and then ether, and dried to provide 360 mg. of 7-[D-α-(4-hydroxynicotinoylamido)-α-phenylacetamido]-3-(4-mercaptopyrimidin-6-yl)thiomethyl-Δ³-cephem-4-carboxylic acid.

Infrared absorption spectrum: $\nu_{max}^{KBr}$cm.$^{-1}$: 1770.

Nuclear magnetic resonance spectra (D₆-DMSO): δ(ppm): 3.52 (2H), 3.98 (1H), 4.42 (1H), 5.02 (1H), 5.76 (2H), 6.46 (1H), 7.16 (1H), 7.36 (5H), 7.84 (1H), 8.20 (1H), 8.46 (1H), 9.46 (1H).

EXAMPLE 6

A mixture of 420 mg. of 7-[D-α-(4-hydroxynicotinoylamido)-α-phenylacetamido]cephalosporanic acid, 240 mg. of 2-amino-4,6-dimercaptopyrimidine, 170 mg. of sodium hydrogencarbonate, and 30 ml. of water was stirred for 22 hours at 55° C. The reaction mixture thus obtained was filtered and 1 normal hydrochloric acid was added to the filtrate under ice cooling to adjust the pH of it to 1. The precipitates formed were recovered by filtration, washed with water and then ether, and dried to provide 410 mg. of 7-[D-α-(4-hydroxynicotinoylamido)-α-phenylactamido]-3-(2-amino-6-mercaptopyridin-4-yl)thiomethyl-Δ³-cephem-4carboxylic acid.

Infrared absorption spectrum: $\nu_{max}^{KBr}$cm.$^{-1}$: 1760.

Nuclear magnetic resonance spectra (D$_6$-DMSO):
δ(ppm): 3.52 (2H), 3.96 (1H), 4.34 (1H), 5.04 (1H), 5.80 (2H), 6.40 (1H), 6.46 (1H), 7.02 (2H), 7.40 (5H), 7.84 (1H), 8.48 (1H), 9.46 (1H).

EXAMPLE 7

A mixture of 530 mg. of 7-[D-α-(4-hydroxynicotinoylamido)-α-phenylacetamido]cephalosporanic acid, 300 mg. of 4,6-dimercapto-2-methylthiopyrimidine, 250 mg. of sodium hydrogencarbonate, and 40 ml. of water was stirred for 22 hours at 55° C. The reaction mixture thus obtained was filtered and 1 normal hydrochloric acid was added to the filtrate under ice cooling to adjust the pH of it to 1. The precipitates formed were recovered by filtration, washed with water and then ether, and dried to provide 590 mg. of 7-[D-α-(4-hydroxynicotinoylamido)-α-phenylacetamido]-3-(4-mercapto-2-methylthiopyrimidin-6-yl)thiomethyl-Δ$^3$-cephem-4-carboxylic acid.

Infrared absorption spectrum: $\nu_{max}^{KBr}$cm.$^{-1}$: 1775.

Nuclear magnetic resonance spectra (D$_6$-DMSO):
δ(ppm): 3.52 (2H), 4.10 (1H), 4.50 (1H), 5.02 (1H), 5.80 (2H), 6.44 (1H), 7.38 (6H), 8.82 (1H), 8.46 (1H), 9.46 (1H). duplicated with 250(3H) DMSO).

What is claimed is:

1. A 7-(α-hydroxy-substituted pyridylcarboxamido-α-phenylacetamido)-3-substituted thiomethyl-Δ$^3$-cephem-4-carboxylic acid derivative represented by the formula:

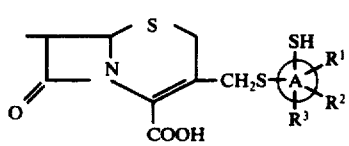

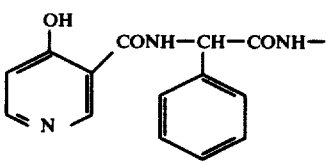

wherein A represents an unsaturated 6-membered ring having one sulfur atom or 2 or 3 nitrogen atoms and the remaining members being carbon atoms and R$^1$, R$^2$, and R$^3$, which may be the same or different, each represents a hydrogen atom, a lower alkyl group, a lower alkylthio group, an amino group, a lower alkanoylamido group, or an oxo group and a pharmacologically acceptable salt thereof.

2. The carboxylic acid derivative as claimed in claim 1 in which said derivative is the 7-(α-hydroxynicotinoylamido-α-phenylacetamido-3-substituted thiomethyl-Δ$^3$-cephem-4-carboxylic acid derivative represented by the formula:

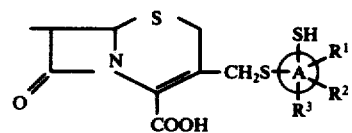

wherein A, R$^1$, R$^2$, and R$^3$ have the same meaning as defined in claim 1.

3. The carboxylic acid derivative as claimed in claim 1 in which said derivative is the 7-(α-4-hydroxynicotinoylamido-α-phenylacetamido)-3-(4-mercapto-substituted pyrimidinylthiomethyl)-Δ$^3$-cephem-4-carboxylic acid derivative represented by the formula

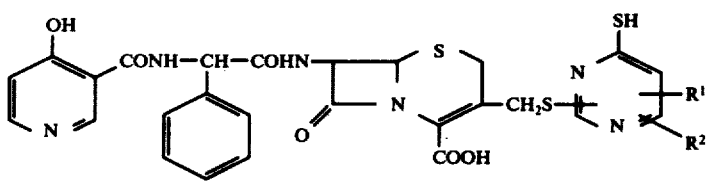

wherein R$^1$ and R$^2$ have the same meaning as defined in claim 1.

4. The carboxylic acid derivative as claimed in claim 1 in which said derivative is the 7-(α-4-hydroxynicotinoylamido-α-phenylacetamido)-3-(4-oxo-4H-substituted thiopyranylthiomethyl)-Δ$^3$-cephem-4-carboxylic acid derivative represented by the formula

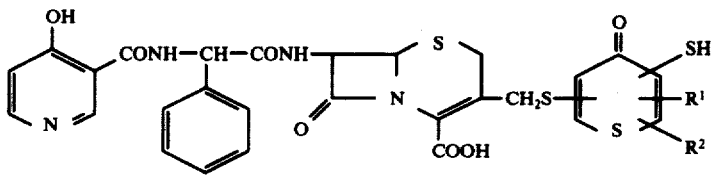

wherein R$^1$ and R$^2$ have the same meaning as defined in claim 1.

5. A carboxylic acid derivative according to claim 1, which is 7-(α-4-hydroxynicotinoylamido-α-phenylacetamido)-3-(4-mercapto-2-methylpyrimidin-6-ylthiomethyl)-Δ$^3$-cephem-4-carboxylic acid and its pharmacologically acceptable salts.

6. A carboxylic acid derivative according to claim 1, which is 7-(α-4-hydroxynicotinoylamido-α-phenylacetamido)-3-(4-mercaptopyrimidin-6-ylthiomethyl)-Δ$^3$-cephem-4-carboxylic acid and its pharmacologically acceptable salts.

7. A carboxylic acid derivative according to claim 1, which is 7-(α-hydroxynicotinoylamido-α- phenylacetamido)-3-(4-mercapto-2-methylthiopyrimidin-6-ylthiomethyl)-Δ³-cephem-4-carboxylic and its pharmacologically acceptable salts.

8. A carboxylic acid derivative according to claim 1, which is 7-(α-4-hydroxynicotinoylamido-α-phenylacetamido)-3-(2-mercapto-3,5-dimethyl-4-oxo-4H-thiopyran-6-ylthiomethyl)-Δ³-cephem-4-carboxylic acid and its pharmacologically acceptable salts.

* * * * *